(12) United States Patent
Guidry

(10) Patent No.: US 11,419,910 B1
(45) Date of Patent: Aug. 23, 2022

(54) TREATMENT OF DERMATITIS AND ATHLETE'S FOOT

(71) Applicant: Guy J. Guidry, Covington, LA (US)

(72) Inventor: Guy J. Guidry, Covington, LA (US)

( * ) Notice: Subject to any disclaimer, the term of this patent is extended or adjusted under 35 U.S.C. 154(b) by 0 days.

(21) Appl. No.: 16/871,952

(22) Filed: May 11, 2020

Related U.S. Application Data

(60) Provisional application No. 62/846,298, filed on May 10, 2019.

(51) Int. Cl.
| | | |
|---|---|---|
| *A61K 33/04* | (2006.01) | |
| *A61K 36/752* | (2006.01) | |
| *A61K 9/08* | (2006.01) | |
| *A61K 9/00* | (2006.01) | |

(52) U.S. Cl.
CPC .......... *A61K 36/752* (2013.01); *A61K 9/0014* (2013.01); *A61K 9/08* (2013.01); *A61K 33/04* (2013.01)

(58) Field of Classification Search
None
See application file for complete search history.

(56) References Cited

U.S. PATENT DOCUMENTS

| | | | | |
|---|---|---|---|---|
| 7,250,174 | B2 * | 7/2007 | Lee | A61P 17/00 424/401 |
| 9,144,576 | B2 | 9/2015 | Brown et al. | |
| 10,232,047 | B2 | 3/2019 | Prasad et al. | |
| 2007/0173424 | A1 * | 7/2007 | Rupert | C11D 9/38 510/141 |
| 2019/0099335 | A1 | 4/2019 | Latta et al. | |
| 2020/0031791 | A1 * | 1/2020 | Du | A61L 15/46 |

FOREIGN PATENT DOCUMENTS

| | | | |
|---|---|---|---|
| CN | 107997983 | * | 5/2018 |
| EP | 0025721 | | 2/1984 |
| WO | 2009/111040 | | 9/2009 |
| WO | 2014/165253 | | 10/2014 |
| WO | 2015/105905 | | 7/2015 |
| WO | 2018/129233 | | 7/2018 |

OTHER PUBLICATIONS

Newbury et al., "Use of lime sulphur and itraconazole to treat shelter cats naturally infected with Microsporum canis in an annex facility: an open field trial," 2007 (https://patents.google.com/scholar/5313241180898903979q=lime&q=sulfur&q=cure&q=fungus&scholar&oq=lime+sulfur+cure+fungus).
Tweedy, "Inorganic sulfur as a fungicide," 1981.
Inorganic sulfur as a fungicide, Residue Reviews pp. 43-68.
Dell, Darin (DVM, DACVD), "A Practical Guide for Talking to Clients about Autoimmune Skin Diseases".
"Lime Sulfur: general purpose Organic fungicide you can make at home," Future Feeders Blog, Oct. 22, 2014.
"Lime Sulfur—general purpose Organic fungicide you can make at home," Agrodragon Co., Ltd.
Gupta, "The use of sulfur in dermatology," Journal of drugs in dermatology, Jul. 2004.
"Lime Sulfur," Small Animal Clinical Pharmacology (Second Edition), 2008.

* cited by examiner

*Primary Examiner* — Ralph J Gitomer
(74) *Attorney, Agent, or Firm* — Garvey, Smith & Nehrbass, Patent Attorneys, L.L.C.; Julie Rabalais Chauvin; Charles C. Garvey, Jr.

(57) ABSTRACT

The present invention relates to a composition and use thereof directed towards treating various health ailments, such as skin and respiratory problems and various infections. More particularly, the present invention relates to a lime sulfur solution and use thereof, of varying percentages, directed towards improving vision and treating various skin problems and infections, such as toenail fungus, athlete's foot, jock itch, skin psoriasis, eczema, vaginal yeast infections, head or beard dandruff, respiratory infections, itching of the skin (particularly of the hands), acne (facial and/or body acne), poison ivy, insect bites, head and body lice, crabs, cuts, treating wounds infected by staff and/or MRSA (methicillin-resistant *Staphylococcus aureus*) bacteria, tongue thrush, ringworm, penis foreskin infections, skin tags, and is also directed towards treating various respiratory infections (such as pneumonia, chronic obstructive pulmonary disease (COPD), asthma, and Covid-19 infections). The present invention also relates to use of the aforementioned composition and solution as a disinfectant in gyms, spas, saunas, for professional athletes, or as a body and/or hair wash.

17 Claims, No Drawings

US 11,419,910 B1

TREATMENT OF DERMATITIS AND ATHLETE'S FOOT

CROSS-REFERENCE TO RELATED APPLICATIONS

This application claims the benefit of my U.S. Provisional Patent Application Ser. No. 62/846,298, filed 10 May 2019, which is hereby incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a composition and use thereof directed towards treating various health ailments, such as skin and respiratory problems and various infections. More particularly, the present invention relates to a lime sulfur solution and use thereof, of varying percentages, directed towards improving vision and treating various skin problems and infections, such as toenail fungus, athlete's foot, jock itch, skin psoriasis, eczema, vaginal yeast infections, head or beard dandruff, respiratory infections, itching of the skin, acne (facial and/or body acne), poison ivy, insect bites, head and body lice, crabs, cuts, wounds infected by staff and/or MRSA (methicillin-resistant *Staphylococcus aureus*) bacteria, tongue thrush, ringworm, penis foreskin infections, skin tags, and is also directed towards treating various respiratory infections (such as pneumonia, chronic obstructive pulmonary disease (COPD), asthma, and Covid-19 infections). The present invention also relates to use of the aforementioned composition and solution as a disinfectant in gyms, spas, saunas, or for professional athletes, or as a body and/or hair wash.

2. General Background of the Invention

The following prior art references relate to the general background of the invention, and are incorporated herein by reference:

U.S. Pat. No. 10,232,047; WO 2009/111040; US 2019/0099335; U.S. Pat. No. 9,144,576; WO 2014/165253; WO 2018/129233; WO 2015/105905; "Inorganic sulfur as a fungicide," Tweedy, Residue Reviews book series (RECT, volume 78), 1981; "Use of lime sulphur and itraconazole to treat shelter cats naturally infected with *Microsporum canis* in an annex facility: an open field trial," Newbury et al., *Veterinary dermatology,* 2007; "Lime Sulfur: general purpose Organic fungicide you can make at home," Future Feeders Blog, 2014; "Lime Sulfur-general purpose Organic fungicide you can make at home," Agrodragon.com; "The use of sulfur in dermatology," Gupta et al., *Journal of drugs in dermatology,* 2004.

BRIEF SUMMARY OF THE INVENTION

The present invention relates to a composition and use thereof directed towards treating various health ailments, such as skin and respiratory problems and various infections. More particularly, the present invention relates to a lime sulfur solution and use thereof, of varying percentages, directed towards improving vision and treating various skin problems and infections, such as toenail fungus, athlete's foot, jock itch, skin psoriasis, eczema, vaginal yeast infections, head or beard dandruff, respiratory infections, itching of the skin (particularly of the hands), acne (facial and/or body acne), poison ivy, insect bites, head and body lice, crabs, cuts, treating wounds infected by staff and/or MRSA (methicillin-resistant *Staphylococcus aureus*) bacteria, tongue thrush, ringworm, penis foreskin infections, skin tags, and is also directed towards treating various respiratory infections (such as pneumonia, chronic obstructive pulmonary disease (COPD), asthma, and Covid-19 infections). The present invention also relates to use of the aforementioned composition and solution as a disinfectant in gyms, spas, saunas, for professional athletes, or as a body and/or hair wash. In various preferred embodiments, the present invention is used to improve vision and treat various skin, respiratory problems and infections in human patients.

DETAILED DESCRIPTION OF THE INVENTION

The present invention relates to a composition and use thereof directed towards treating various health ailments, such as skin and respiratory problems and various infections. More particularly, the present invention relates to a lime sulfur (lime sulphur) solution and use thereof, of varying percentages, directed towards improving vision and treating various skin and respiratory problems and infections, such as toenail fungus, athlete's foot, jock itch, skin psoriasis, eczema, vaginal yeast infections, head or beard dandruff, respiratory infections, itching of the skin (including of the hands), acne (facial and/or body acne), poison ivy, insect bites, head and body lice, crabs, cuts, treating wounds infected by staff and/or MRSA (methicillin-resistant *Staphylococcus aureus*) bacteria, tongue thrush, ringworm, penis foreskin infections, skin tags, and is also directed towards treating various respiratory infections (such as pneumonia, chronic obstructive pulmonary disease (COPD), asthma, and Covid-19 infections). The present invention also relates to use of the aforementioned composition and solution as a disinfectant in gyms, spas, saunas, for professional athletes, or as a body and/or hair wash. In various preferred embodiments, the present invention is used to improve vision and treat various skin, respiratory problems and infections in human patients.

In various preferred embodiments, the present invention includes the following lime sulfur (lime sulphur) composition: a composition which can be made using 20 kg of pure sulphur, 10 kg of hydrated lime or "quick lime", and 100 L of water, preferably distilled water, which yields approximately 3.5 to 4 gallons of lime sulfur solution. Alternative compositions include those which can be made with 1-100 kg pure sulphur, 0.5-100 kg hydrated lime, and 1-1000 L of water; alternative compositions also include those which can be made with 2-50 kg pure sulphur, 1-100 kg hydrated lime, and 2-500 L of water; alternative compositions also include those which can be made with 5-30 kg pure sulphur, 5-30 kg hydrated lime, and 5-150 L of water.

In various preferred embodiments, the present invention includes the following method of preparing the lime sulfur composition: bring the water to a boil; separately, mix the sulfur with a small amount of water, preferably room temperature distilled water, to form a paste; add all the lime at once to the boiling distilled water and stir until it is dissolved; add the sulfur paste slowly to the lime and boiled water mixture; cook the mixture preferably for approximately eight (8) hours preferably stirring the mixture continuously; add boiling distilled water to the already boiling mixture to maintain a constant 100 L of mixture to compensate for evaporation; let the mixture settle overnight; and the mixture can then be placed into various containers when cooled, preferably completely.

In various preferred embodiments, soaps, water, fragrances, oil, essential oils, lava, charcoal, oatmeal and/or glycerin soap can be mixed into the lime sulphur composition of the present invention, preferably to treat skin and respiratory problems and infections and to improve vision preferably in human patients. Examples of essential oils that can be used are: Roman Chamomile, Hyssop, *eucalyptus*, Lavender, Rose, Vetiver, Ylang Ylang, Frankincense, Peppermint, Spearmint, Cedarwood, Lemon, Basil Oil, Orange, Grapefruit, Wintergreen, *Cassia*, and Oregano.

In various preferred embodiments, the present invention can be used to treat toenail and fingernail fungus. (Toenail fungus can include fungi dermatophytes, such as *candida, tinea*, yeasts and molds, such as *Trichophyton Rubrum*.) In various preferred embodiments of the present invention, toenail and fingernail fungus can be treated in human patients preferably using an approximately 30-75% solution of the aforementioned lime sulfur composition (preferably diluting the aforementioned lime sulfur composition with enough water to produce an approximate 30-75% solution), adding aromas and essential oils, and applying this liquid solution preferably on a daily basis to the infected area (such as the toenail and fingernail), preferably for approximately 3-6 months. In various preferred embodiments of the present invention, a 3-6% solution bar soap form of the aforementioned lime sulfur composition (preferably diluting the aforementioned lime sulfur composition with enough water to produce an approximate 3-6% solution for bar soap form) is used preferably about twice a week in the shower to supplement treatment. In various preferred embodiments, the present invention can also include adding aromas and/or essential oils to mask the odor of the lime sulphur. When adding aromas and/or essential oils to the solution, add approximately 2-20 mL per 12 oz of the aforementioned lime sulphur composition. Essential Oils that can be used include, but are not limited to: Roman Chamomile, Hyssop, *eucalyptus*, Lavender, Rose, Vetiver, Ylang Ylang, Frankincense, Peppermint, Spearmint, Cedarwood, Lemon, Basil Oil, Orange, Grapefruit, Wintergreen, *Cassia*, and Oregano. Treatment with the addition of essential oils to various preferred embodiments of the present invention preferably includes applying this liquid solution preferably on a daily basis, preferably for approximately 3-6 months.

In various preferred embodiments, the present invention can be used to treat athlete's foot (also known as *Tinea pedis*). In various preferred embodiments of the present invention, athlete's foot can be treated in human patients preferably using an approximately 1-10% solution of the aforementioned lime sulfur composition (preferably diluting the aforementioned lime sulfur composition with enough water to produce approximately a 1-10% solution), and applying either a liquid form of this solution or a bar soap form of this solution. In various preferred embodiments, the present invention can treat athlete's foot in human patients by applying the composition on a daily basis. In various preferred embodiments, the present invention can treat athlete's foot in human patients by applying the composition every other day. In various preferred embodiments, the lime composition to treat athlete's foot is applied to the troubled area and then pat dry or by soaking the infected foot in this solution until symptoms are alleviated.

In various preferred embodiments, the present invention can be used to treat psoriasis and/or eczema and/or a fungal infection caused by *candida*. In various preferred embodiments of the present invention, psoriasis and/or eczema and/or a fungal infection caused by *candida* can be treated in human patients preferably using an approximately 1-5% solution of the aforementioned lime sulfur composition (preferably diluting the aforementioned lime sulfur composition with enough water to produce an approximate 1-5% solution), and applying either a liquid form of this solution or a bar soap form of this solution preferably twice a week preferably in the shower until symptoms are alleviated.

In various preferred embodiments, the present invention can be used to treat jock itch (also known as *Tinea cruris*). In various preferred embodiments of the present invention, jock itch can be treated in human patients preferably using an approximately 3% solution of the aforementioned lime sulfur composition (preferably diluting the aforementioned lime sulfur composition with enough water to produce approximately a 3% solution), and applying either a liquid form of this solution or a bar soap form of this solution preferably twice a week preferably in the shower until symptoms are alleviated.

In various preferred embodiments, the present invention can be used to treat vaginal yeast infections. In various preferred embodiments of the present invention, vaginal yeast infections can be treated in human patients preferably using an approximately 3% solution of the aforementioned lime sulfur composition (preferably diluting the aforementioned lime sulfur composition with enough water to produce approximately a 3% solution), and applying either a liquid form of this solution or a bar soap form of this solution preferably twice a week preferably in the shower until symptoms are alleviated.

In various preferred embodiments, the present invention can be used to treat head and/or beard dandruff. In various preferred embodiments of the present invention, head and/or beard dandruff can be treated in human patients preferably using an approximately 3-6% solution of the aforementioned lime sulfur composition (preferably diluting the aforementioned lime sulfur composition with enough water to produce approximately a 3-6% solution), and applying either a liquid form of this solution or a bar soap form of this solution preferably twice a week preferably in the shower until symptoms are alleviated. In various preferred embodiments, the present invention can also stop hair loss.

In various preferred embodiments, the present invention can be used to treat facial acne, such as facial acne caused by fungus or *staphylococcus* bacteria or by an overgrowth of yeast in hair follicles. In various preferred embodiments of the present invention, facial acne can be treated in human patients preferably using an approximately 3-6% solution of the aforementioned lime sulfur composition (preferably diluting the aforementioned lime sulfur composition with enough water to produce approximately a 3-6% solution), and applying either a liquid form of this solution or a bar soap form of this solution preferably twice a day until symptoms are alleviated.

In various preferred embodiments, the present invention can be used to treat body acne, such as body acne caused by fungus or *staphylococcus* bacteria or by an overgrowth of yeast in hair follicles. In various preferred embodiments of the present invention, body acne can be treated in human patients preferably using an approximately 3% solution of the aforementioned lime sulfur composition (preferably diluting the aforementioned lime sulfur composition with enough water to produce approximately a 3% solution), and applying either a liquid form of this solution or a bar soap form of this solution preferably twice a day until symptoms are alleviated.

In various preferred embodiments, the present invention can be used to treat poison ivy and/or insect bites. In various preferred embodiments of the present invention, poison ivy and/or insect bites can be treated in human patients preferably using an approximately 0.05-10% solution of the aforementioned lime sulfur composition (preferably diluting the aforementioned lime sulfur composition with enough water to produce approximately a 0.05-10% solution), and applying a liquid form of this solution preferably 1-2 times daily until symptoms are alleviated.

In various preferred embodiments, the present invention can be used to treat body and head lice and/or crabs. In various preferred embodiments of the present invention, head lice and/or crabs can be treated in human patients preferably using an approximately 3-10% solution of the aforementioned lime sulfur composition (preferably diluting the aforementioned lime sulfur composition with enough water to produce approximately a 3-10% solution), and applying either a liquid form or bar soap form of this solution preferably twice a week for 2 weeks, preferably until symptoms are alleviated.

In various preferred embodiments, the present invention can be used to treat cuts and/or wounds infected with *staphylococcus* bacteria, such as MRSA. In various preferred embodiments of the present invention, cuts and/or wounds infected with *staphylococcus* bacteria, such as MRSA, can be treated in human patients preferably using an approximately 3-100% solution of the aforementioned lime sulfur composition (preferably diluting the aforementioned lime sulfur composition with enough water to produce approximately a 3-100% solution), and applying this solution preferably directly to the wound or cut. In various preferred embodiments of the present invention, the lime sulfur treatment of wounds and/or cuts can include zero additional oils or fragrances.

In various preferred embodiments, the present invention can be used to treat oral or tongue thrush (also known as oral candidiasis). In various preferred embodiments of the present invention, oral or tongue thrush can be treated in human patients preferably using an approximately 0.5-3% solution of the aforementioned lime sulfur composition (preferably diluting the aforementioned lime sulfur composition with enough water to produce approximately a 0.5-3% solution) as a mouthwash. In various preferred embodiments of the present invention, this treatment of oral or tongue thrush can include zero additional oils or fragrances.

In various preferred embodiments, the present invention can be used to treat ringworm. In various preferred embodiments of the present invention, ringworm can be treated in human patients preferably using an approximately 10-50% solution of the aforementioned lime sulfur composition (preferably diluting the aforementioned lime sulfur composition with enough water to produce approximately a 10-50% solution), and applying this solution directly to the ringworm.

In various preferred embodiments, the present invention can be used to treat penis foreskin infections, such as those caused by fungus balanoposthitis. In various preferred embodiments of the present invention, penis foreskin infections can be treated in human patients preferably using an approximately 1-5% solution of the aforementioned lime sulfur composition (preferably diluting the aforementioned lime sulfur composition with enough water to produce an approximately 1-5% solution), pulling back the foreskin, and washing with this approximately 1-5% solution in a bar or liquid soap form. In various preferred embodiments of the present invention, this treatment of penis foreskin infections can include essential oils and fragrances.

In various preferred embodiments, the present invention can be used to treat respiratory infections. More specifically, the present invention can be used to treat fungal or bacterial respiratory infections, such as pneumonia, COPD, or asthma. In various preferred embodiments of the present invention, respiratory infections can be treated in human patients preferably using an approximately 0.5-10% solution of the aforementioned lime sulfur composition (preferably diluting the aforementioned lime sulfur composition with enough water to produce an approximately 0.5-10% solution), and then preferably breathing this solution in as a vapor/steamer inhalant.

In various preferred embodiments, the present invention can be used to treat infections caused by the coronavirus (also known as Covid-19). In various preferred embodiments of the present invention, infections caused by Covid-19 can be treated in human patients preferably using an approximately 0.5-10% solution of the aforementioned lime sulfur composition (preferably diluting the aforementioned lime sulfur composition with enough water to produce an approximately 0.5-10% solution), and then preferably breathing this solution in as a vapor/steamer inhalant.

In various preferred embodiments, the present invention can be used as a body and/or hair wash of humans preferably using an approximately 0.5-10% solution of the aforementioned lime sulfur composition (preferably diluting the aforementioned lime sulfur composition with enough water to produce an approximately 0.5-10% solution) and applying either a liquid form of this solution or a bar soap form of this solution daily or several times a week for a fully body deep cleanse. In various preferred embodiments of the present invention, this body and/or hair wash can include essential oils and fragrances.

In various preferred embodiments, the present invention can be used as a disinfectant, for example, as a disinfectant at gyms, spas, or saunas. Various preferred embodiments of the present invention can be used as a disinfectant using an approximately 1-20% solution of the aforementioned lime sulfur composition (preferably diluting the aforementioned lime sulfur composition with enough water to produce an approximately 1-20% solution). In various preferred embodiments of the present invention, this disinfectant can include essential oils and fragrances.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:
1. A method of treating athlete's foot in a subject in need of treatment, comprising applying to the skin of the subject a bar soap having a lime sulfur composition,
   wherein the lime sulfur composition is made using the following ratios of ingredients:
   1-100 kg pure sulfur,
   0.5-100 kg hydrated lime, and
   1-1000 L of water, and the lime sulfur composition is diluted to make said bar soap.

2. The method of claim 1, wherein a solution of about 1-5% of the lime sulfur composition is used to make the bar soap.

3. The method of claim 1, wherein the lime sulfur composition is made using the following ratios of ingredients:
2-50 kg pure sulfur,
1-100 kg hydrated lime, and
2-500 L of water.

4. The method of claim 3, wherein the lime sulfur composition is made using the following ratios of ingredients:
5-30 kg pure sulfur,
5-30 kg hydrated lime, and
5-150 L of water.

5. The method of claim 3, wherein a solution of about 1-5% of the lime sulfur composition is used to make the bar soap.

6. A method of treating dermatitis in a subject in need of treatment, comprising applying to the skin of the subject a lime sulfur composition,
wherein the lime sulfur composition is made using the following ratios of ingredients:
1-100 kg pure sulfur,
0.5-100 kg hydrated lime, and
1-1000 L of water.

7. The method of claim 6, wherein the lime sulfur composition is made using the following ratios of ingredients:
2-50 kg pure sulfur,
1-100 kg hydrated lime, and
2-500 L of water.

8. The method of claim 7, wherein the lime sulfur composition is made using the following ratios of ingredients:
5-30 kg pure sulfur,
5-30 kg hydrated lime, and
5-150 L of water.

9. The method of claim 8, wherein the dermatitis is athlete's foot, and a solution of about 1-5% of the lime sulfur composition is applied.

10. The method of claim 6, wherein the dermatitis is athlete's foot, and a solution of about 1-5% of the lime sulfur composition is applied.

11. A method of treating dermatitis in a subject in need of treatment, comprising applying to the skin of the subject a bar soap having a lime sulfur composition,
wherein the lime sulfur composition is made using the following ratios of ingredients:
1-100 kg pure sulfur,
0.5-100 kg hydrated lime, and
1-1000 L of water, and
the lime sulfur composition is diluted and used to make said bar soap.

12. The method of claim 11, wherein about a 1-5% solution of the lime sulfur composition is used to make the bar soap.

13. The method of claim 11, wherein the lime sulfur composition is made using the following ratios of ingredients:
2-50 kg pure sulfur,
1-100 kg hydrated lime, and
2-500 L of water.

14. The method of claim 13, wherein about a 1-5% solution of the lime sulfur composition is used to make the bar soap.

15. The method of claim 11, wherein the lime sulfur composition is made using the following ratios of ingredients:
5-30 kg pure sulfur,
5-30 kg hydrated lime, and
5-150 L of water.

16. The method of claim 15, wherein about a 1-5% solution of the lime sulfur composition is used to make the bar soap.

17. The method of claim 15, wherein the dermatitis is athlete's foot and a solution of about 1-5% of the lime sulfur composition is used to make the bar soap.

* * * * *